(12) United States Patent
Farrell

(10) Patent No.: US 12,005,198 B2
(45) Date of Patent: Jun. 11, 2024

(54) PACKAGED HYDROPHILIC MEDICAL DEVICES

(71) Applicant: Hollister Incorporated, Libertyville, IL (US)

(72) Inventor: David J Farrell, Ballina (IE)

(73) Assignee: Hollister Incorporated, Libertyville, IL (US)

( * ) Notice: Subject to any disclaimer, the term of this patent is extended or adjusted under 35 U.S.C. 154(b) by 241 days.

(21) Appl. No.: 17/612,948

(22) PCT Filed: May 21, 2020

(86) PCT No.: PCT/US2020/034011
§ 371 (c)(1),
(2) Date: Nov. 19, 2021

(87) PCT Pub. No.: WO2020/237057
PCT Pub. Date: Nov. 26, 2020

(65) Prior Publication Data
US 2022/0226602 A1 Jul. 21, 2022

Related U.S. Application Data

(60) Provisional application No. 62/851,425, filed on May 22, 2019.

(51) Int. Cl.
*A61M 25/00* (2006.01)
*B65B 5/08* (2006.01)
*B65B 31/00* (2006.01)

(52) U.S. Cl.
CPC ............ *A61M 25/002* (2013.01); *B65B 5/08* (2013.01); *B65B 31/00* (2013.01); *A61M 2205/0222* (2013.01); *A61M 2207/00* (2013.01)

(58) Field of Classification Search
CPC .... B65D 81/20; B65D 81/32; B65D 81/3272; B65B 5/08; B65B 31/00; A61M 25/002;
(Continued)

(56) References Cited

U.S. PATENT DOCUMENTS 4,596,713 A * 6/1986 Burdette ............ B65D 81/3469
426/107
4,627,986 A * 12/1986 Bardsley ............ B65D 81/3222
206/217

(Continued)

FOREIGN PATENT DOCUMENTS

EP 2060296 A1 5/2009
WO 2005014055 A1 2/2005
(Continued)

OTHER PUBLICATIONS

International Search Report and Written Opinion dated Sep. 16, 2020 for International Application No. PCT/US2020/034011.

*Primary Examiner* — Chun Hoi Cheung
*Assistant Examiner* — Brijesh V. Patel
(74) *Attorney, Agent, or Firm* — Cook Alex Ltd.

(57) ABSTRACT

Ready to use packaged medical products that include hydrated hydrophilic medical devices and methods of making the same. The packed medical product includes a package defining a cavity with a first compartment and a second compartment separated by a vapor permeable, liquid impermeable barrier. A hydrophilic medical device is contained within the first compartment, and a liquid is contained in the second compartment. The liquid produces a vapor that migrates through the vapor permeable, liquid impermeable barrier into a first compartment. The second compartment has a pressure that is greater than the pressure in the first compartment.

20 Claims, 2 Drawing Sheets

(58) Field of Classification Search
CPC ........ A61M 25/0017; A61M 2205/022; A61M 2207/00
USPC ....... 206/219, 571, 438, 210, 364, 439, 561; 604/265, 172, 544; 53/425–426, 431, 53/452, 469, 474, 478
See application file for complete search history.

(56) References Cited

U.S. PATENT DOCUMENTS

| | | | | |
|---|---|---|---|---|
| 5,456,929 | A * | 10/1995 | Mifune | B65D 81/3222 426/106 |
| 7,159,374 | B2 | 1/2007 | Abercrombie et al. | |
| 7,163,967 | B2 | 1/2007 | Grah et al. | |
| 7,922,984 | B2 * | 4/2011 | Hamilton | A61L 2/20 206/568 |
| 8,919,553 | B2 * | 12/2014 | Murray | A61M 25/002 604/172 |
| 2003/0098149 | A1 | 5/2003 | Wellington et al. | |
| 2004/0123563 | A1 | 7/2004 | Inada et al. | |
| 2005/0070882 | A1 * | 3/2005 | McBride | A61M 25/002 206/571 |
| 2005/0109648 | A1 * | 5/2005 | Kerzman | A61M 25/0111 206/364 |
| 2006/0263404 | A1 * | 11/2006 | Nielsen | A61M 25/0045 424/422 |
| 2007/0080078 | A1 * | 4/2007 | Hansen | B65D 81/3266 206/219 |
| 2009/0240214 | A1 * | 9/2009 | Conway | A61M 25/002 206/572 |
| 2011/0056852 | A1 * | 3/2011 | Frojd | B65B 5/04 206/364 |
| 2011/0114520 | A1 * | 5/2011 | Matthison-Hansen | A61M 25/0111 206/364 |
| 2012/0316515 | A1 * | 12/2012 | Terry | A61M 25/007 604/257 |
| 2013/0174600 | A1 * | 7/2013 | Sarcinella | F25D 5/02 126/263.08 |
| 2014/0190846 | A1 * | 7/2014 | Belt | A61L 29/085 53/431 |
| 2015/0297861 | A1 | 10/2015 | Passalaqua et al. | |
| 2016/0136391 | A1 | 5/2016 | Foley et al. | |
| 2017/0152066 | A1 | 6/2017 | Kawashima | |

FOREIGN PATENT DOCUMENTS

| | | | |
|---|---|---|---|
| WO | 2007076154 A2 | 7/2007 | |
| WO | 2014074142 A1 | 5/2014 | |
| WO | 2014093056 A1 | 6/2014 | |
| WO | 2014142895 A1 | 9/2014 | |
| WO | 2015065725 A1 | 5/2015 | |
| WO | 2018156502 A2 | 8/2018 | |
| WO | WO-2018156502 A2 * | 8/2018 | ............... A61L 2/08 |
| WO | 2018227066 A1 | 12/2018 | |
| WO | 2020106812 A1 | 5/2020 | |

* cited by examiner

PACKAGED HYDROPHILIC MEDICAL DEVICES

The present application is the U.S. National Stage Application of PCT Application No. PCT/US2020/034011, filed May 21, 2020, which claims the benefit of and priority to U.S. Provisional Application No. 62/851,425, filed May 22, 2019, both of which are hereby incorporated herein by reference.

DESCRIPTION

Field of the Disclosure

The present disclosure generally relates to packaged hydrophilic medical products and methods of hydrating medical products within the package. Even more particularly, the present disclosure relates to packaged hydrophilic catheter assemblies and methods of hydrating the same.

Background

It is desirable for medical devices that are inserted into the body to have a lubricated or lubricious outer surface to facilitate insertion into and/or removal of the medical device from the body. Such devices may include, for example, urinary catheters, endoscopes, cardiovascular catheters, syringes, vascular stents, etc. Such medical devices may have a hydrophilic coating or layer disposed on an outer surface thereof. Hydrophilic coatings are becoming the preferred method of providing lubricious surfaces because of their high lubricity and ease of use. Hydrophilic coatings become slippery or lubricous when wetted with a hydration medium, such as saline or liquid or vapor water. The hydrated lubricous hydrophilic coating eases insertion and removal of the device, which can result in minimizing soft tissue damage and reducing overall discomfort during use of the medical device.

When a hydrophilically coated medical device is used, the hydrophilic coating is hydrated with a hydration medium prior to use to activate the hydrophilic coating. It is advantageous for the hydrophilic coating to be hydrated within the package so that the device is ready-to-use right out of the package without the user having to activate the hydrophilic coating prior to use.

Therefore, there remains a need for improved packaged hydrophilic medical devices.

SUMMARY

In one aspect, a packaged medical device product includes a package defining a cavity. The cavity includes a first compartment and a second compartment wherein the first and second compartments are separated by a vapor permeable, liquid impermeable barrier. The product also includes a hydrophilic medical device contained within the first compartment. The hydrophilic medical device including a hydrophilic material that becomes lubricious when hydrated. A liquid is contained in the second compartment. The liquid produces a vapor that migrates through the vapor permeable, liquid impermeable barrier into a first compartment, whereby the vapor hydrates the hydrophilic material. The pressure in the second compartment is greater than the pressure in the first compartment.

A method of making a package medical device product including placing hydrophilic medical device in first compartment of package. A vapor producing liquid is placed in a second compartment of the package. The first compartment and the second compartment are separated by a vapor permeable, liquid impermeable barrier. The package is closed and the pressure is increased in the second compartment.

DETAILED DESCRIPTION OF THE EMBODIMENTS

Figure 1:
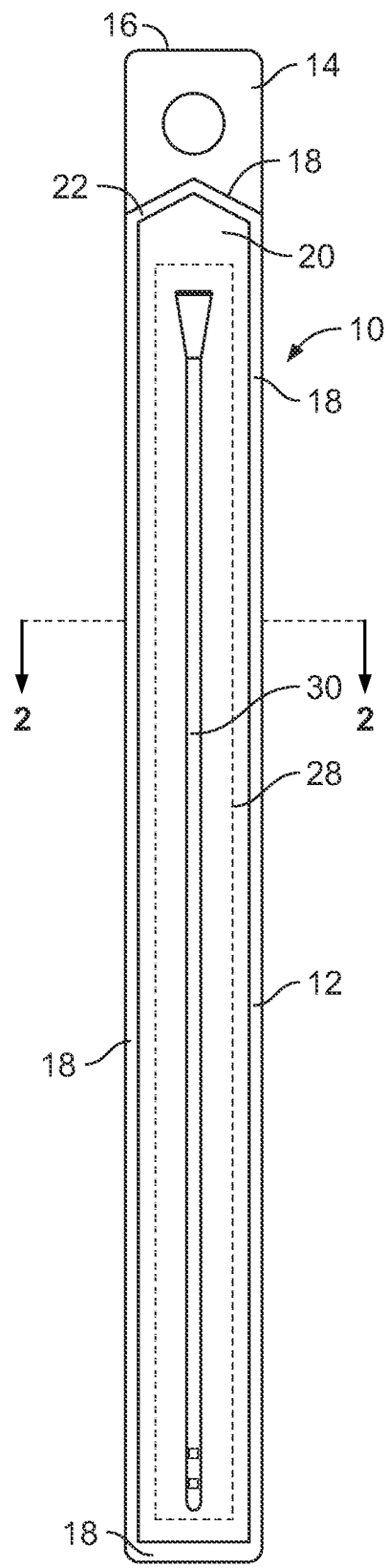
FIG. 1 is a top plan view of one embodiment of a packaged medical device in accordance with the present disclosure.
Figure 2:
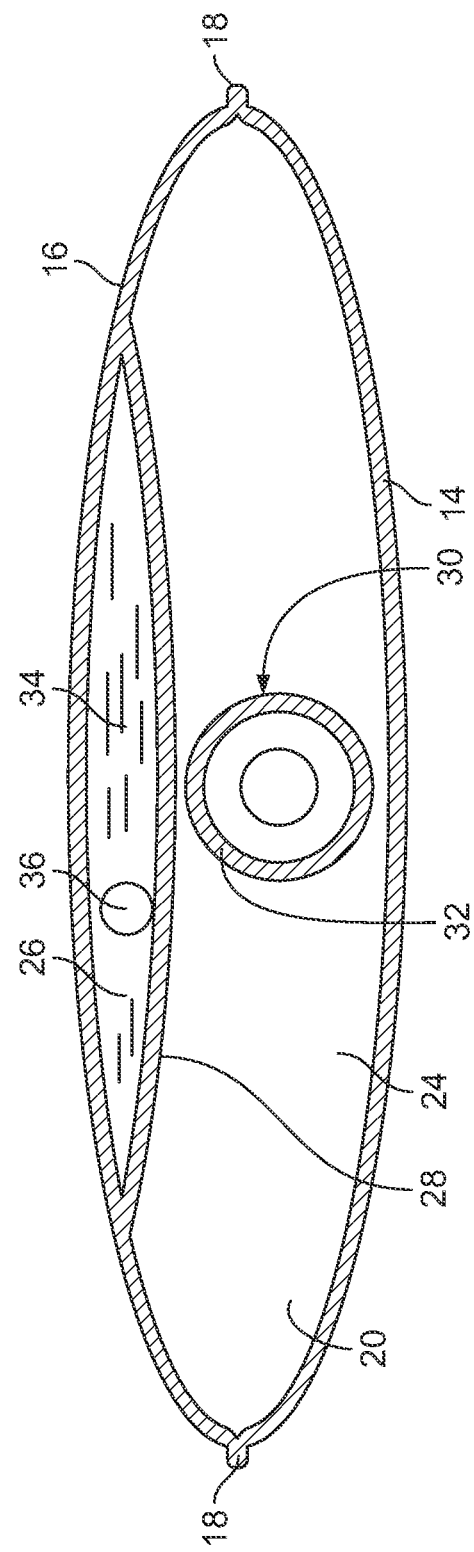
FIG. 2 is cross-sectional view of the packaged medical device of FIG. 1, taken along lines 2-2.

The present disclosure is generally directed to packaged hydrophilic medical products 10 that are ready to use right out of the package. Referring to FIGS. 1 and 2, the packaged hydrophilic medical product 10 includes a package 12. In the illustrated embodiment, the package 12 is formed from a front sheet 14 and back sheet 16 that are sealed together to form a peripheral seal 18 and define an internal cavity 20. At the top of the package 12, the front and back sheets 14 and 16 may be unattached above top seal 22. The package may be opened by grasping these unattached portions and pulling the front sheet 14 and back sheet 16 from each other to peal open the package 12 along peripheral seal 18. Optionally, the package 12 may be any other suitable package for containing a medical device such as a tear open package. Additionally, the material of the package, optionally, may be made from a gas impermeable material.

As shown in FIG. 2, the internal cavity 20 of the package is divided into a first compartment 24 and a second compartment 26. The first and second compartments 24 and 26 are separated by a vapor permeable, liquid impermeable barrier 28, such as a sheet or film. Optionally, the barrier may be a vapor permeable calcium carbonate film. The barrier 28 may be adhered to or sealed to the back sheet 16 such that the second compartment is defined between the barrier 28 and the back sheet 16.

A hydrophilic medical device is contained within the first compartment 24. In the illustrated embodiment, a hydrophilic catheter 30 is contained within the first compartment 24. The hydrophilic catheter 30 may be any suitable hydrophilic catheter that includes a hydrophilic outer surface 32 that becomes lubricous when hydrated with a hydration medium, such as water. For example, the catheter 30 may include a lubricious hydrophilic coating on the outer surface of the catheter 30.

The second compartment 26 contains a liquid 34, such as liquid water or an aqueous solution, which produces or donates a vapor (such as water vapor). The vapor produced in the second compartment 28 by the liquid 34 migrates through the vapor permeable, liquid impermeable barrier 28 and moves into the first compartment 24. In the first compartment 24, the vapor contacts the hydrophilic material 32 of the catheter 30 to hydrate the hydrophilic material 32.

Referring to FIG. 2, the second compartment 26 includes a mechanism for increasing gas pressure within the second compartment 26. This increase in gas pressure in the second compartment 26 results in the gas pressure of the second compartment 26 being greater than the gas pressure in the first compartment 24, thereby creating a pressure gradient across the vapor permeable, liquid impermeable barrier 28 and a gas pressure differential between the first and second compartments 24 and 26. This pressure gradient assists in increasing the rate of migration of the vapor from the second compartment 26 into the first compartment 24. That is, when the pressure in the second compartment 26 is greater than that of the first compartment 24, the flow of the vapor from the second compartment 26 to the first compartment 24 is increased. Thus, more vapor enters the first compartment 24 in a shorter period of time than if there was no pressure gradient between the compartments 24 and 26. With more vapor entering the first compartment 24 in a shorter period of time, the hydrophilic material 32 hydrates faster than when there is no pressure gradient between the compartments 24 and 26.

The mechanism for creating a pressure gradient includes a mechanism that produces a pressure increasing gas in the second compartment 26. The mechanism may produce carbon dioxide, oxygen, nitrogen, etc. Optionally, the pressure increasing mechanism may include mixing of two or more components that react to produce the gas. For example, the components may be acid and a carbonate that react to produce a carbon dioxide. In one example, the mechanism may include mixing sodium bicarbonate and citric acid. As explained in more detail below, the components may be in solution and/or in solid form. For example, the acid and carbonate may be water soluble components that are included in the vapor producing liquid 34. Referring to FIG. 2, one of the acid or carbonate may be placed in the package in solid form 36, such as in tablet or powder form. The other of the components may be included in the liquid 34. When the packaged device assembly 10 is formed, the solid form 36 is placed in the second compartment 26 along with the liquid 34 that contains the other of the components.

Alternately, again referring to FIG. 2, both the acid and carbonate may be placed in the package in solid form 36, such as in tablet or powder form. When the packaged device assembly 10 is formed, the solid form 36 is placed in the second compartment 26 along with the liquid 34. When the solid form 36 is wetted by the liquid 34 the reaction between the acid and carbonate proceeds, thereby producing a gas.

The catheter 30 is placed in the first compartment 24 and the package 10 is closed and sealed. The two components react with one another to produce a gas, thereby increasing the pressure within the second compartment 26.

In another embodiment, the first component is included in a first liquid to form a first solution and the second component is included in a second liquid to form a second solution. During packaging, the first and second solutions are placed in the second compartment 24 and the catheter 30 is sealed within the package in a similar manner as described above. When the solutions come into contact with each other, the first and second components react to produce a gas, thereby increasing the pressure in the second compartment 24. With a gas pressure gradient formed, the vapor produced by the liquid 34 will migrate at a faster rate across the barrier 28, than if there was no pressure gradient.

It should be understood that various changes and modifications to the presently preferred embodiments described herein will be apparent to those skilled in the art. Such changes and modification can be made without departing from the spirit and scope of the invention disclosed herein.

What is claimed is:

1. A packaged medical product, comprising:
a package defining a cavity, the cavity including a first compartment and a second compartment wherein the first and second compartments are separated by a vapor permeable, liquid impermeable barrier;
a hydrophilic medical device contained within the first compartment, the hydrophilic medical device including a hydrophilic material that becomes lubricious when hydrated;
a liquid contained in the second compartment, the liquid producing a vapor that migrates through the vapor permeable, liquid impermeable barrier into a first compartment, whereby the vapor hydrates the hydrophilic material; and
wherein the second compartment has a pressure that is greater than a pressure in the first compartment.

2. The packaged medical product of claim 1, wherein the second compartment includes a pressure increasing mechanism.

3. The packaged medical product of claim 2, wherein the pressure increasing mechanism comprises components that react with each other to produce a gas.

4. The packaged medical product of claim 3, wherein the components comprise a first component and a second component, and wherein one of the first and second components comprises an acid and the other of the first component and the second component comprises a carbonate.

5. The packaged medical product of claim 4, wherein the acid comprises citric acid and the carbonate comprises sodium bicarbonate.

6. The packaged medical product of claim 4, wherein the first component is in a first solution and the second component is in a second solution, and the first solution and the second solution are mixed to form the liquid.

7. The packaged medical product of claim 4, wherein the first component is in solid form and the second component is in the liquid.

8. The packaged medical product of claim 4, wherein the first component and the second component are in solid form.

9. The packaged medical product of claim 4, wherein the gas comprises one or more of carbon dioxide, nitrogen and oxygen.

10. The packaged medical product of claim 1, wherein the hydrophilic medical device comprises a urinary catheter.

11. A method of making a packaged medical product, comprising:
placing a hydrophilic medical device in a first compartment of a package;
placing a vapor producing liquid in a second compartment of the package, wherein the first compartment and the second compartment are separated by a vapor permeable, liquid impermeable barrier;
closing the package; and
increasing pressure in the second compartment.

12. The method of claim 11, further including the step of placing a pressure increasing mechanism in the second compartment.

13. The method of claim 12, wherein the pressure increasing mechanism comprises components that react with each other to produce a gas.

14. The method of claim 13, wherein the components comprise a first component and a second component, and wherein one of the first and second components comprises an acid and the other of the first component and the second component comprises a carbonate.

15. The method of claim 14 wherein the acid comprises citric acid and the carbonate comprises sodium bicarbonate.

16. The method of claim 14, wherein the first component is in a first solution and the second component is in a second solution, and the first solution and the second solution are mixed to form the liquid.

17. The method of claim 14, wherein the first component is in solid form and the second component is in the liquid.

18. The method of any claim 14, wherein the first component and second component are in solid form.

19. The method of claim 13, wherein the gas comprises one or more of carbon dioxide, nitrogen and oxygen.

20. The method of claim 11, wherein the hydrophilic medical device comprises a urinary catheter.

* * * * *